(12) United States Patent
Russell et al.

(10) Patent No.: US 6,361,201 B1
(45) Date of Patent: Mar. 26, 2002

(54) CENTRALIZED BICARBONATE MIXING SYSTEM

(75) Inventors: Richard M. Russell, Brentwood; Michael J. Peterson, Nashville, both of TN (US)

(73) Assignee: Dialysis Systems, Inc., Nashville, TN (US)

( * ) Notice: Subject to any disclaimer, the term of this patent is extended or adjusted under 35 U.S.C. 154(b) by 0 days.

(21) Appl. No.: 09/586,094

(22) Filed: Jun. 2, 2000

Related U.S. Application Data

(60) Provisional application No. 60/137,647, filed on Jun. 4, 1999.

(51) Int. Cl.[7] ............................. B01F 5/10; B01F 13/00; B01F 15/06
(52) U.S. Cl. ...................................... 366/144; 366/136
(58) Field of Search ................................ 366/136, 144, 366/163.2, 184, 165.1; 210/646, 647

(56) References Cited

U.S. PATENT DOCUMENTS

| | | | |
|---|---|---|---|
| 3,326,815 A | | 6/1967 | Werner et al. ............... 252/314 |
| 4,007,921 A | * | 2/1977 | Zingg .......................... 366/136 |
| 4,202,760 A | * | 5/1980 | Storey et al. |
| 4,756,838 A | * | 7/1988 | Veltman |
| 4,863,277 A | | 9/1989 | Neal et al. ................... 366/137 |
| 5,015,389 A | | 5/1991 | Portillo, Jr. ................. 210/646 |
| 5,211,475 A | * | 5/1993 | McDermott ............... 366/163.2 |
| 5,344,231 A | | 9/1994 | Jonsson et al. ............. 366/137 |
| 5,476,320 A | * | 12/1995 | Taguchi et al. ............. 366/137 |
| 5,616,248 A | | 4/1997 | Schal ......................... 210/647 |
| 5,727,877 A | * | 3/1998 | Chevallet et al. ........... 366/137 |
| 5,779,355 A | * | 7/1998 | Pullman .................. 366/163.2 |

* cited by examiner

Primary Examiner—Tony G. Soohoo
(74) Attorney, Agent, or Firm—Waddey & Patterson; Lucian Wayne Beavers

(57) ABSTRACT

A centralized bicarbonate mixing system is provided for a plurality of dialysis machines of a dialysis clinic. The system includes a source of purified water, a mix tank, an eductor having a hopper for receiving dry bicarbonate material, a mixing pump and a mixing conduit loop connecting the mixing pump, the eductor and the mix tank so that as water is circulated by the mixing pump through the mixing conduit loop, the dry bicarbonate material is drawn into the eductor and mixed with the water. The system further includes a circulation tank, and a transfer conduit connecting the mixing conduit loop to the circulation tank, so that a mixed bicarbonate solution can be transferred from the mixing conduit loop to the circulation tank. The system further includes a circulation pump, and a circulation supply conduit connecting the circulation tank and the circulation pump so that mixed bicarbonate solution can be pumped from the circulation tank to the dialysis machines. The system is preferably constructed of cross-linked polyethylene and/or polypropylene plastic pipe and fittings, and is provided with heat exchangers so that the same can be heat disinfected. Furthermore, the use of the eductor and closed hopper allows for easy loading of dry bicarbonate material into the system, and for sanitary mixing of a batch of bicarbonate solution in the closed system.

21 Claims, 4 Drawing Sheets

CENTRALIZED BICARBONATE MIXING SYSTEM

This application claims benefit of our Provisional U.S. Patent Application Serial No. 60/137,647 filed Jun. 4, 1999.

Be it known that we, Richard M. Russell, a citizen of the United States, residing in Brentwood, Tenn.; and Michael J. Peterson, a citizen of the United States, residing in Nashville, Tenn. have invented a new and useful "Centralized Bicarbonate Mixing System."

BACKGROUND OF THE INVENTION

1. Field of the Invention

The present invention relates generally to apparatus for mixing additives and water for medical purposes, and more particularly, but not by way of limitation, to apparatus for mixing a bicarbonate solution for use with dialysis machines.

2. Description of the Prior Art

Conventional prior art centralized mixing systems have used a mixing tank into which water was directed and into which bulk quantities of powered additives have been dumped into the open top of the tank. The water and dry additives are then mixed through the use of a mechanical mixer. The mixed solution is then pumped to a storage tank from which it is delivered to the individual dialysis machines.

There are several problems with such systems. First, the mixing tank is typically an open top tank which allows the mixture to be contaminated which leads to medical complications for the patients using the mixture. Second, it is physically difficult to lift the large bags of bulk material into the open top tank, and the operation of this equipment leads to many on-the-job injuries, such as back strains and the like.

Centralized bicarbonate systems are frequently cited as the source of water born bacteria and endotoxin. This probably results from the enhancement in the growing medium permeate solution typically has too little nutrient to support bacteria growth) and the fact that the system is open for charging and mixing for extended periods of time.

One other system which has been more recently developed to provide preparation of fluid concentrates is that shown in U.S. Pat. No. 5,344,231 to Jonsson, et al. The Jonsson, et al. system utilizes a cartridge apparatus for the mixing of concentrate and water at the immediate location of the dialysis machine. The primary difficulty with the Jonsson, et al. system is its high cost.

Thus, it is seen that there is a need in the art for improved systems for mixing of water and additives for medical uses, and particularly to provide bicarbonate solution to dialysis machines, while eliminating the problems of the various prior art systems discussed above.

SUMMARY OF THE INVENTION

The present invention provides a system for mixing water and an additive to form a concentrate solution. The system includes a mix tank having an outlet. A pump has a suction inlet connected to the outlet of the mix tank, and has a pump discharge. An eductor has a fluid inlet and a fluid outlet with a flow path connecting the fluid inlet and the fluid outlet. The eductor has an eductor inlet connected to the flow path. The fluid inlet of the eductor is connected to the pump discharge. An additive container has an outlet connected to the eductor inlet, so that additive stored in the additive container is drawn therefrom by the flow of fluid through the flow path of the eductor. A return line connects the fluid outlet of the eductor to the mix tank. Thus, a closed system is provided in which water and the dry additives may be mixed by a combination of the mixing activity which takes place in the eductor and the piping downstream of the eductor and by further mixing action which takes place as the mixture is re-circulated back through the mix tank.

The present invention is developed to reduce the opportunity for having an open tank while preparing dialysate and to make the mixing process more ergonomic and faster. This is accomplished by reducing the height of the port for charging the solid bicarbonate powder, using a funnel and ejector to wet and mix the powder with circulating permeate and agitating the mix tank with nozzles driven by the re-circulating flow of fluid.

It is therefore a general object of the present invention to provide an improved system for mixing water and additives to form concentrate solutions for medical uses.

Still another object of the present invention is the provision of an additive mixing system which is completely closed so as to prevent contamination of the solution.

Yet another object of the present invention is to provide a system for mixing water and additives which does not require bags of additive powder to be lifted overhead into large mixing tanks.

Still another object of the present invention is the provision of systems for mixing water and additives which are economical.

Other and further objects, features and advantages of the present invention will be readily apparent to those skilled in the art upon reading of the following disclosure when taken in conjunction with the accompanying drawings.

DETAILED DESCRIPTION OF THE PREFERRED EMBODIMENTS

Figure 1:
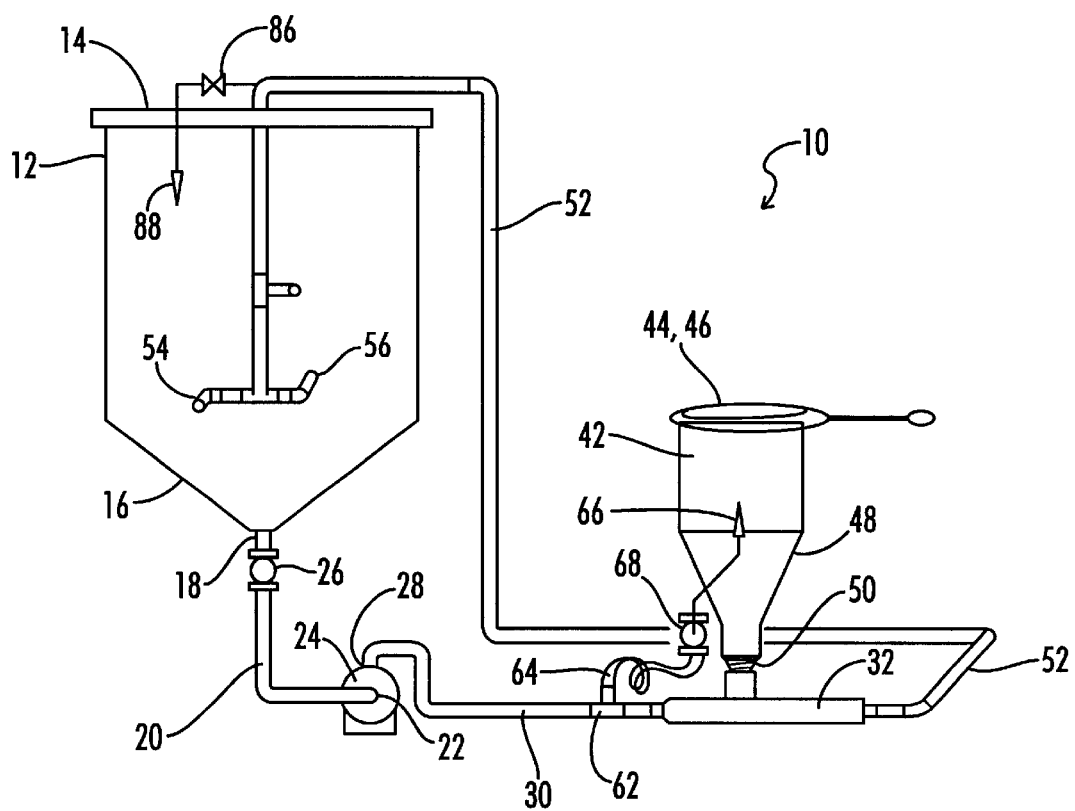
FIG. 1 is an isometric view of the mixing system of the present invention.

Referring now the drawings, and particularly to FIG. 1, the system of the present invention is shown and generally designated by the numeral 10. The system 10 may be described as a system for mixing water and an additive to form a concentrate solution, and more particularly, as a system for mixing a permeate solution with a dry additive powder such as sodium bicarbonate to provide a sodium bicarbonate solution to be utilized by dialysis machines in a dialysis clinic.

The system 10 as shown in FIG. 1 includes a mix tank 12. The mix tank 12 has a closed top 14 and a conical bottom 16 leading to a mix tank outlet 18.

An outlet line 20 is connected to the outlet 18 and to a suction inlet 22 of a pump 24. A valve 26 is located in the outlet line 20.

The pump 24 is a conventional centrifugal pump which takes fluid in the suction inlet 22 and discharges the fluid at a pump discharge 28.

The pump discharge outlet 28 is connected to a discharge line 30 which leads to an eductor 32. The eductor 32 may for example be a "Jet Pump" as available from the Penberthy Company of Prophetstown, Ill.

Figure 4:
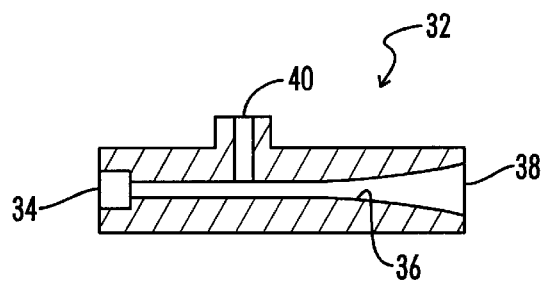
FIG. 4 is an enlarged sectioned schematic view of the eductor of the system of FIGS. 1 and 2.

A schematic cross-sectional view of the eductor 32 is shown in FIG. 4. The eductor 32 includes a fluid inlet 34 which is connected by a flow path 36 to a fluid outlet 38. An eductor inlet 40 is laterally connected to the flow path 36 so that fluid flowing through the flow path 36 from the inlet 34 to the outlet 38 draws a suction on the eductor inlet 40 which will, in turn, draw material into the eductor 32.

An additive container or hopper 42 is mounted on top of the eductor 32. The additive container has a top 44 which may be closed by a rotatable hatch 46. The additive container includes a conical shaped bottom portion 48 leading to a container outlet 50 which is connected to the eductor inlet 40 so that additive material stored in the additive container 42 is drawn therefrom by the flow of fluid through the flow path 36 of the eductor 32.

Upstream of the eductor inlet 34 there is a tee 62 contained in the discharge line 30. The tee 62 is connected to a wash-down line 64 which leads to a clean in place nozzle 66 located within the additive container 42 for washing down the same. A valve 68 in the wash-down line 64 controls the flow of fluid to the clean in place nozzle 66.

A return line 52 is connected to the outlet 38 of eductor 32 and returns to the mix tank 12.

The return line 52 leads to a pair of offset laterally directed ejection nozzles 54 and 56 disposed in the mix tank 12, so that fluid returned to the mix tank 12 creates a swirling action in the mix tank to further mix the water and additive within the mix tank 12.

The return line 52 also leads via valve 86 to a clean in place nozzle 88 located within the mix tank 12 for aiding in cleaning the same.

It will be appreciated that the system 10 is a closed system. As will be further described below with regard to FIG. 2, permeate or water is provided to the tank 12 from a source and then is circulated through the system 10 in which the additive, which is placed in additive tank 42, is mixed with the permeate to provide the desired concentrate solution. As further described below with regard to FIG. 2, the concentrate solution can then be directed to a storage and circulation tank from which it will be provided to the individual dialysis machines.

Figure 2:
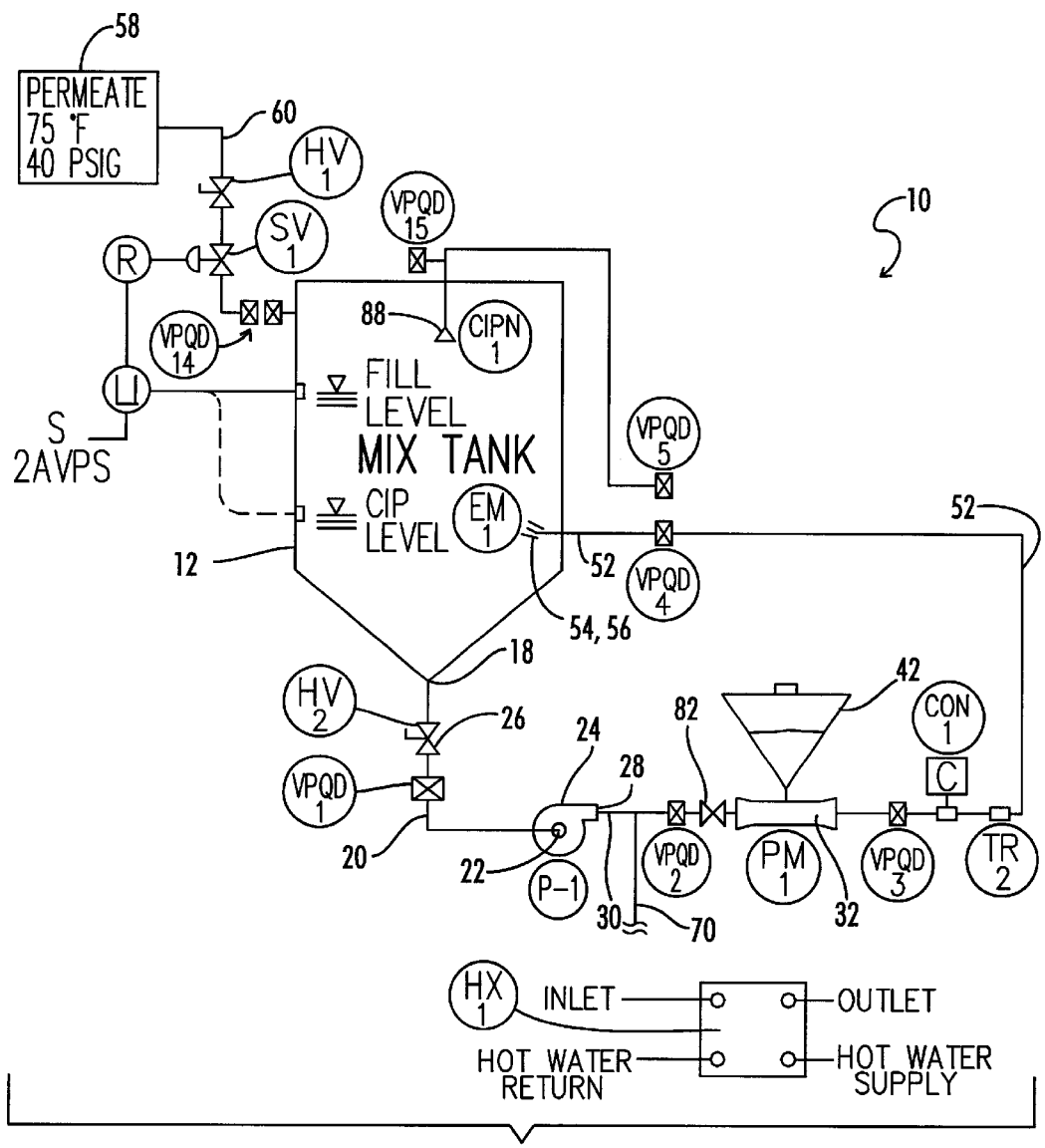
FIG. 2 is a schematic illustration of the mixing system of FIG. 1.

Turning now to FIG. 2, the system 10 of FIG. 1 is there schematically illustrated and other details of the system are schematically illustrated.

The water or permeate solution which is to be mixed with the additive is provided from a source 58 via supply line 60.

Figure 3:
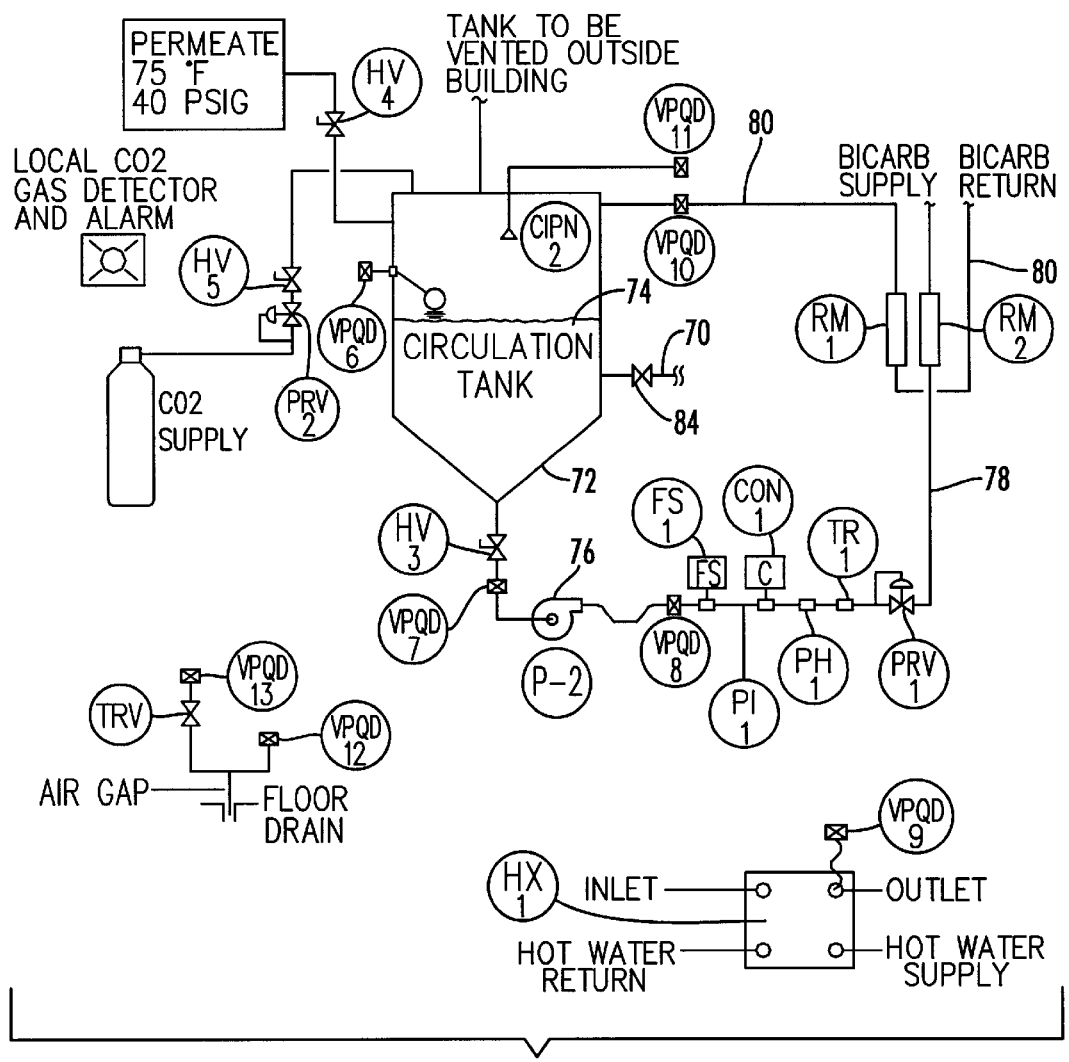
FIG. 3 is a schematic illustration of a circulation tank and fluid supply piping which is utilized with the mixing system of FIG. 2.

In the discharge line 30 there is a takeoff line 70 which is connected to a circulation tank 72 of FIG. 3. The circulation tank 72 serves as a central storage tank from which the bicarbonate solution may be supplied to a series of dialysis machines in a dialysis clinic. The bicarbonate solution 74 contained in the circulation tank 72 is pumped by a pump 76 to a bicarbonate supply line 78 which leads to the dialysis machines and flows in a loop returning as bicarbonate return line 80 to the circulation tank 72.

In general, the system of FIGS. 1 and 2 is operated in the following manner.

Permeate or water is provided from source 58 via supply line 60 to the sealed mix tank 12. The fluid is pumped from the mix tank 12 via pump 24 through the eductor 32 and then back through the return line 52, thus providing a closed circulating fluid flow loop. The desired quantity of dry additive material is placed in the additive container 42 and is fed therefrom into the eductor 32. The additive mixes with the fluid in the eductor 32 and the discharge line 52 and further mixes as it circulates through the mix tank 12 where it is swirled due to the action of the ejector nozzles 54 and 56.

The desired volume of water and additives such as sodium bicarbonate are mixed in the circulating system 10 until they are satisfactorily mixed.

For example, one suitable formula for mixing a batch of bicarbonate solution is as follows. To make 50 gallons of solution, utilize 189.25 liters of permeate, 12.48 kilograms of NAHCO3 premix power, and 4.46 kilograms of NACL.

When a batch is satisfactorily mixed, it may be directed to the circulation tank 74 by closing a valve 82 and opening a valve 84. As soon as the batch of bicarbonate solution has been pumped into the tank 72, the valve 82 is reopened and the valve 84 is closed.

Then the system 10 will be cleaned by washing the same with clean fluid, and the process can be repeated to make a new batch of bicarbonate solution in the system 10 and then once again direct it to the circulation tank 72.

It will be understood that the circulation tank 72 serves as a place for storage of the mixed bicarbonate solution, and subsequent supply of the same as needed to the individual dialysis machines.

DETAILED DESCRIPTION OF OPERATION AND HEAT

DISINFECTION OF MIX TANK SYSTEM OF FIG. 2

To fill the mix tank 12 the following steps are conducted:
1. The mounting position for the capacitance switch cut off is selected for the desired volume of solution in the tank;
2. The valve designated HV2 is closed;
3. The valve HV1 is opened;
4. The "on" switch is depressed thus opening the normally closed solenoid valve designated SV1;
5. The tank 12 is allowed to fill.

The operation of mixing the dry bicarbonate powder from hopper 42 includes generally the following steps:
1. The desired amount of pre-mixed NAHCO3 is added to hopper 42 as required by the volume of solution to be mixed and the formula to be used;
2. The top of the hopper 42 is closed with lid 46;
3. Valve HV2 is opened and the circulation pump 24 is turned on. Note that the discharge line 52 must be connected to the tank 12 through the valve ported quick disconnect designated as VPQD4;
4. The permeate solution is circulated through the mixing loop until all of the dry powder material from hopper 42 is completely dissolved;
5. After complete dissolution, the powder mixer 32, 42 can be removed from the circulation loop on the fly with the pump 24 running by connecting VPQD2 to VPQD3;
6. The mix tank 12 can remain circulating until it is desired to transfer its contents to the bicarbonate circulation tank 72;

7. The powder mixer 32, 42 should be flushed with permeate and allowed to drain and dry.

The sequence of operations for transferring bicarbonate solution from the mix tank 12 to the circulation tank 74 can be generally described as follows:

1. Disconnect VPQD4 and make connection to VPQD6 on the circulation tank 72;
2. Empty the mix tank 12 into the circulation tank 72;
3. Disconnect VPQD6 and reconnect to VPQD4;
4. Turn pump 24 off.

The sequence of operations for cleaning in place the system of FIG. 2 and heat disinfecting the same generally includes the following:

1. Turn the capacitance level switch to the low level clean in place setting;
2. Depress the fill switch, opening the permeate feed solenoid SV1;
3. Connect VPQD2 to heat exchanger HX-1 inlet;
4. Connect VPQD3 to heat exchanger HX-1 outlet;
5. Turn circulation pump 24 on;
6. After 30 minutes, break connection at VPQD4 and make connection at VPQD5 to flow fluid to clean in place nozzle 88;
7. Circulate water for at least 15 minutes and preferably about one-half hour, maintaining temperature above 190° F.;
8. Break connection at VPQD5 and reconnect at drain air gap; and
9. Run contents to drain.

The normal operation of the circulating tank 72 in FIG. 3 is to continuously circulate via pump 76 through the bicarbonate supply line 78 to the loop piping system directed to the dialysis clinic, which returns through bicarbonate return line 80.

When it is desired to heat clean in place the system of FIG. 3, the sequence of operations is generally as follows:

1. The remaining solution is drained from tank 72 and from the loop piping by breaking connection VPQD-10 and reconnecting to the air gap drain;
2. After solution has been drained, the loop piping and tank 72 are filled with permeate, circulating the permeate with pump 76. After filling the tank with approximately 100 gallons of permeate, the permeate fill valve HV-4 is closed;
3. The connection at VPQD8 is broken and the circulation is routed through heat exchanger HX-1;
4. The heated permeate is circulated until the temperature reaches 190° F. and is continued for 30 minutes;
5. The connection at VPQD10 is broken and then the connection at VPQD11 is made, thus circulating the hot permeate through clean in place nozzle designated as CIPN2;
6. The permeate is circulated in the manner described for 30 minutes, maintaining the temperature above 190° F.;
7. The connection at DPQD11 is broken and connected to VPQD13;
8. The contents are run to the drain. The draining of the system in this manner will result in siphoning of the residual permeate from the pump 76 and associated piping. No dialysis machines or other devices which could either receive hot permeate or give up contaminated fluids can be connected to the bicarbonate loops while the clean in place operations are being performed. VPQD13 is connected to a bimetallic temperature solenoid valve with a closing set point of 85° F. This functions to purge the hot disinfection fluid from the system, without loss of cooler permeate that may be used as a flushing agent. VPQD12 is provided as an open drain connection without proof of temperature for discharge; and
9. VPQD10 is reconnected and the circulation tank 72 is filled from the mix tank 12 through VPQD6 as previously described.

THE EMBODIMENT OF FIG. 5

Figure 5:
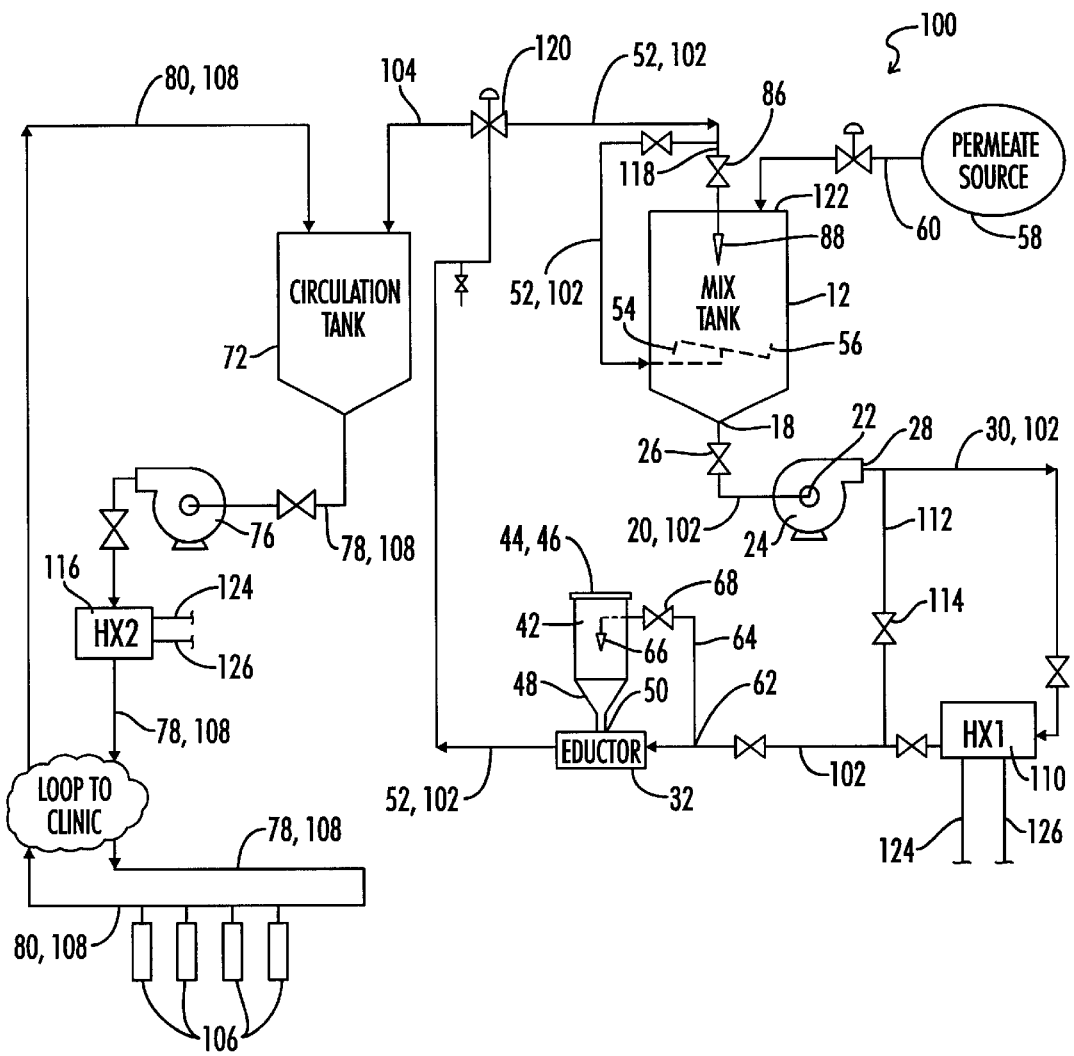
FIG. 5 is a schematic illustration of a modified embodiment of the invention showing the mixing system, along with the circulation system and the dialysis clinic.

Turning now to FIG. 5, a modified embodiment is shown of the mixing system of the present invention is shown and generally designated by the numeral 100. Many of the components of the system 100 are substantially identical to those of the system 10 previously described, and like numerals are used to identify the same.

The system 100 can be summarized as follows. The system includes a source 58 of purified water, the mix tank 12, the eductor 32 having hopper 42, and a mixing pump 24. The system further includes a mixing loop 102 which connects the mix pump 24, the eductor 32 and the mix tank 12. The mixing loop 102 includes the discharge line 30, the return line 52, the outlet line 20, and the various items of equipment located therein.

The system 10 further includes a transfer conduit 104 connecting the mixing conduit loop 102 to the circulation tank 72, so that a mixed bicarbonate solution can be transferred from the mixing conduit loop 102 to the circulation tank 72.

The system 100 further includes the circulation pump 76 and the circulation supply conduit 78 which leads from the circulation tank 72 to the circulation pump 76 and on to the plurality of dialysis machines 106.

The system 100 further includes the circulation return conduit 80 for returning unused mixed bicarbonate solution from the dialysis machines 106 to the circulation tank 72.

The circulation supply conduit 78 and the return conduit 80 define a circulation loop 108 which also includes the various items of equipment disposed within the circulation loop 108.

A first heat exchanger 110 is disposed in the mixing conduit loop 102 so that mixing conduit loop 102, the mix tank 12, the eductor 32 and the mix pump 24 can be heat disinfected by circulating heated water through the mixing conduit loop 102.

The system 100 further includes a bypass line 112 disposed in the mixing conduit loop 102 and bypassing the first heat exchanger 110. A bypass valve 114 is disposed in the bypass line 112.

A second heat exchanger 116 is disposed in the circulation loop 108 so that the circulation loop 108, the circulation tank 72 and the circulation pump 76 can be heat disinfected by circulating heated water through the circulation loop 108.

The system 100 includes the wash down nozzle 66 disposed in the hopper 42. A wash down line 64 connects the mixing conduit loop 102 to the wash down nozzle 66.

As previously noted, a pair of laterally offset oppositely directed nozzles 54 and 56 are located inside the mix tank 12 and are connected to the mixing conduit loop 102 to create a swirling flow of water and bicarbonate material within the mix tank 12 to mix the water and bicarbonate material thoroughly. The pair of nozzles 54 and 56, and the piping connecting the same to the mixing conduit loop 102 are schematically shown in FIG. 5. It will be understood that the nozzles 54 and 56 preferably line a generally horizontal plane and are pointed 180° apart so as to create a swirling flow in plan view when looking down into the tank 12.

There is also a wash down nozzle 88 in the mix tank 12, and a wash down line 118 connecting the mixing conduit loop 102 to the wash down nozzle 88.

A three-way control valve 120 is disposed in the mixing conduit loop 102 and connects the mixing conduit loop 102 to the transfer conduit 104. The control valve 120 may be selectively moved between a first position wherein flow goes through the mixing conduit loop 102, and a second position wherein flow goes from the mix pump 24 and mixing loop 102 through the transfer line 104 to the circulation tank 72 in order to transfer a batch of bicarbonate solution from the mix tank 12 to the circulation tank 72.

The mixing tank 12 preferably has a closed top 122 to prevent contamination of the fluid mixture contained therein.

The top opening 44 of the hopper 42 is preferably located no greater than about twenty-four to forty-eight inches above the floor from which the hopper 42 is supported. This allows a person operating the system 100 to easily fill the hopper 42 without back strain or the like.

Each of the first and second heat exchangers are connected to a hot water supply, such as a boiler by supply and return lines 124 and 126. The heat exchangers 110 and 116 may be described as permanently located within the circulation loop of the system 100, as contrasted to the system 10 of FIGS. 1, 2 and 3 wherein the analogous hot water heaters are not permanently installed, but rather are located adjacent the system and must be temporarily connected through the use of flexible conduits and quick connect couplings.

It will be understood that the first and second heat exchangers 110 and 116 are not in operation during the normal operation of the system 100 when bicarbonate solution is being mixed and provided to the dialysis machines 106.

It is desirable, however, to periodically heat disinfect the system 100. The mixing conduit loop 102 and the various components disposed therein can be heat disinfected separate from the circulation conduit loop 108. The first heat exchanger 110 is utilized to heat disinfect the mixing conduit loop 102, and the second heat exchanger 116 is utilized to heat disinfect the circulation conduit loop 108.

When it is desired to disinfect the mixing conduit loop 102, the bicarbonate solution is drained from the mix tank 12 and the eductor 32 and the various other components connected to the mixing conduit loop 102. Then the mix tank 12 is at least partially filled with clean permeate. The permeate is heated by circulating the same through the first heat exchanger 110 while simultaneously circulating hot steam or hot water through the dirty side of heat exchanger 110 by means of hot water supply and return conduits 124 and 126. The permeate is heated to a temperature of at least 190° F. and is then circulated through the mixing conduit loop 102 for at least 15 minutes and preferably about one-half hour, thereby disinfecting the mixing tank 12, the eductor 32, the mixing conduit loop 102, and the various other components contained therein.

Similarly, when it is desired to heat disinfect the circulating loop 108 and the various components contained therein, the bicarbonate solution is drained therefrom and then the circulation loop including the circulation tank 72 is filled with clean permeate. That permeate is heated by means of the second heat exchanger 116, which receives heat from steam or hot water passing through the hot water supply in return lines 124 and 126. Then the heated permeate is circulated through the circulation loop 108 at a temperature of at least 190° F. for a time of at least 15 minutes and preferably about one-half hour.

All of the tanks, conduits and the like of system 100 are preferably constructed of cross-lined polyethylene and/or polypropylene plastic material. Further details of preferred heat disinfection methods are disclosed in our application Ser. No. 09/458,140 filed on Dec. 9, 1999 entitled "Heat Disinfection of a Water Supply", the details of which are incorporated herein by reference.

It will be appreciated that in its broadest embodiment, the system 100 discloses a method of providing bicarbonate solution from a centralized source 72 to a plurality of dialysis machines 106. That method includes providing the closed mixing conduit loop 102 and the additive container 42 connected to the mixing conduit loop 102. The container 42 has the open top or loading opening 44 which can be selectively closed by closeable cover 46.

A pre-determined quantity of the dry bicarbonate material is placed through the loading opening 44 into the additive container 42 and the top 46 is then closed.

A pre-determined volume of liquid, such as clean permeate, is circulated in the mixing conduit loop 102. As the pre-determined volume of liquid is circulated, the dry bicarbonate material is transferred from the closed additive container 42 into the circulating liquid in the closed mixing conduit loop 102, thus dissolving the dry bicarbonate material in the circulating permeate.

Circulation is continued and the dry bicarbonate material is continuously drawn into the circulating liquid until the entire pre-determined quantity of dry bicarbonate material is transferred from container 42 into the circulating conduit loop 102 and is dissolved in the pre-determined volume of permeate liquid, thereby producing a batch of bicarbonate solution according to a pre-determined formula.

Then the batch of solution is transferred to the central supply tank or circulation tank 72 from which it may be provided through circulation loop 108 to the plurality of dialysis machines 106.

Although in this specific embodiment disclosed herein, the dry additive container 42 is a hopper associated with an eductor 32, it will be appreciated that in the broader sense of the invention other types of closed dry additive supplies could be utilized with the closed mixing conduit loop 102. For example, dry additive material could be provided via a hopper and auger conveyor into a mixing tank in place of the eductor 32.

Thus, it is seen that the apparatus and methods of the present invention readily achieve and ends and advantages mentioned as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:

1. A centralized bicarbonate mixing system for a plurality of dialysis machines of a dialysis clinic, comprising:
   a source of purified water;
   a mix tank;
   an eductor having a hopper for receiving dry bicarbonate material;

a mixing pump;

a mixing conduit loop connecting the mixing pump, the eductor and the mix tank, the mixing conduit loop being connected to the source of purified water so that as water is circulated by the mixing pump through the mixing conduit loop, the dry bicarbonate material is drawn into the eductor and mixed with the water;

a circulation tank;

a transfer conduit connecting the mixing conduit loop to the circulation tank, so that a mixed bicarbonate solution can be transferred from the mixing conduit loop to the circulation tank;

a circulation pump;

a circulation supply conduit connecting the circulation tank and the circulation pump, so that mixed bicarbonate solution can be pumped from the circulation tank to the dialysis machines; and a heat exchanger disposed in the mixing conduit loop, so that the mixing conduit loop, the mix tank, the eductor and the mixing pump can be heat disinfected by circulating heated water through the mixing conduit loop.

2. The system of claim 1, further comprising a bypass line disposed in the mixing conduit loop and bypassing the heat exchanger.

3. The system of claim 1, further comprising:

a circulation return conduit for returning unused mixed bicarbonate solution from the dialysis machines; the circulation supply and return conduits defining a circulation loop; and a second heat exchanger disposed in the circulation loop, so that the circulation loop, the circulation tank and the circulation pump can be heat disinfected by circulating heated water through the circulation loop.

4. The system of claim 1, further comprising:

a wash down nozzle disposed in the hopper; and a wash down line connecting the mixing conduit loop to the wash down nozzle.

5. The system of claim 1, further comprising:

a pair of laterally off set oppositely directed nozzles located inside the mixing tank and connected to the mixing conduit loop to create a swirling flow of water and bicarbonate material within the mix tank to mix the water and the bicarbonate material.

6. The system of claim 1, further comprising:

a wash down nozzle disposed in the mix tank; and a wash down line connecting the mixing conduit loop to the wash down nozzle.

7. The system of claim 1, further comprising:

a three-way control valve connecting the mixing conduit loop to the transfer conduit.

8. The system of claim 1, further comprising:

the mix tank being closed to prevent contamination of the fluid mixture contained therein.

9. The system of claim 1, wherein:

the hopper has a top opening located no greater than 48 inches above a floor from which the hopper is supported.

10. A system for mixing water and an additive to form a concentrate solution, comprising:

a mix tank having an outlet;

a pump having a suction inlet connected to the outlet of the mix tank, and having a pump discharge;

an eductor, having a fluid inlet, a fluid outlet, a flow path connecting the fluid inlet and fluid outlet and having an eductor inlet connected to the flow path, the fluid inlet being connected to the pump discharge;

an additive container having an outlet connected to the eductor inlet, so that additive stored in the additive container is drawn therefrom by the flow of fluid through the flow path of the eductor;

a return line connected between the fluid outlet of the eductor and the mix tank; and offset laterally directed ejection nozzles disposed in the mix tank and connected to the return line, so that fluid returned to the mix tank creates a swirling action in the mix tank to further mix the water and the additive.

11. The system of claim 10, further comprising:

the mix tank being a closed tank to prevent contamination of the fluid mixture contained therein.

12. The system of claim 10, further comprising:

a hot water source connected to the mixing system so that hot water can be circulated through the mixing system to heat disinfect the mix tank, the pump, the eductor and the additive container.

13. The system of claim 10, further comprising:

a circulation tank for storing mixed concentrate solution;

a transfer line for transferring mixed concentrate solution from the mix tank to the circulation tank; and at least one control valve for allowing the flow of the mixed concentrate solution to the circulation tank.

14. The system of claim 13, further comprising:

a hot water source connected to the mixing system so that hot water can be circulated through the mixing system to heat disinfect the circulation tank.

15. A centralized bicarbonate mixing system for a plurality of dialysis machines of a dialysis clinic, comprising:

a source of purified water;

a mix tank;

an eductor having a hopper for receiving dry bicarbonate material;

a mixing pump;

a mixing conduit loop connecting the mixing pump, the eductor and the mix tank, the mixing conduit loop being connected to the source of purified water so that as water is circulated by the mixing pump through the mixing conduit loop, the dry bicarbonate material is drawn into the eductor and mixed with the water;

a circulation tank;

a transfer conduit connecting the mixing conduit loop to the circulation tank, so that a mixed bicarbonate solution can be transferred from the mixing conduit loop to the circulation tank;

a circulation pump;

a circulation supply conduit connecting the circulation tank and the circulation pump, so that mixed bicarbonate solution can be pumped from the circulation tank to the dialysis machines;

a circulation return conduit for returning unused mixed bicarbonate solution from the dialysis machines, the circulation supply and return conduits defining a circulation loop; and a heat exchanger disposed in the circulation loop, so that the circulation loop, the circulation tank and the circulation pump can be heat disinfected by circulating heated water through the circulation loop.

16. A centralized bicarbonate mixing system for a plurality of dialysis machines of a dialysis clinic, comprising:

a source of purified water;

a mix tank;

an eductor having a hopper for receiving dry bicarbonate material;

a mixing pump;

a mixing conduit loop connecting the mixing pump, the eductor and the mix tank, the mixing conduit loop being connected to the source of purified water so that as water is circulated by the mixing pump through the mixing conduit loop, the dry bicarbonate material is drawn into the eductor and mixed with the water;

a circulation tank;

a transfer conduit connecting the mixing conduit loop to the circulation tank, so that a mixed bicarbonate solution can be transferred from the mixing conduit loop to the circulation tank;

a circulation pump;

a circulation supply conduit connecting the circulation tank and the circulation pump, so that mixed bicarbonate solution can be pumped from the circulation tank to the dialysis machines;

a wash down nozzle disposed in the hopper; and a wash down line connecting the mixing conduit loop to the wash down nozzle.

17. A centralized bicarbonate mixing system for a plurality of dialysis machines of a dialysis clinic, comprising:

a source of purified water;

a mix tank;

an eductor having a hopper for receiving dry bicarbonate material;

a mixing pump;

a mixing conduit loop connecting the mixing pump, the eductor and the mix tank, the mixing conduit loop being connected to the source of purified water so that as water is circulated by the mixing pump through the mixing conduit loop, the dry bicarbonate material is drawn into the eductor and mixed with the water;

a circulation tank;

a transfer conduit connecting the mixing conduit loop to the circulation tank, so that a mixed bicarbonate solution can be transferred from the mixing conduit loop to the circulation tank;

a circulation pump;

a circulation supply conduit connecting the circulation tank and the circulation pump, so that mixed bicarbonate solution can be pumped from the circulation tank to the dialysis machines; and a pair of laterally off set oppositely directed nozzles located inside the mixing tank and connected to the mixing conduit loop to create a swirling flow of water and bicarbonate material within the mix tank to mix the water and the bicarbonate material.

18. A centralized bicarbonate mixing system for a plurality of dialysis machines of a dialysis clinic, comprising:

a source of purified water;

a mix tank;

an eductor having a hopper for receiving dry bicarbonate material;

a mixing pump;

a mixing conduit loop connecting the mixing pump, the eductor and the mix tank, the mixing conduit loop being connected to the source of purified water so that as water is circulated by the mixing pump through the mixing conduit loop, the dry bicarbonate material is drawn into the eductor and mixed with the water;

a circulation tank;

a transfer conduit connecting the mixing conduit loop to the circulation tank, so that a mixed bicarbonate solution can be transferred from the mixing conduit loop to the circulation tank;

a circulation pump;

a circulation supply conduit connecting the circulation tank and the circulation pump, so that mixed bicarbonate solution can be pumped from the circulation tank to the dialysis machines;

a wash down nozzle disposed in the mix tank; and a wash down line connecting the mixing conduit loop to the wash down nozzle.

19. A centralized bicarbonate mixing system for a plurality of dialysis machines of a dialysis clinic, comprising:

a source of purified water;

a mix tank;

an eductor having a hopper for receiving dry bicarbonate material;

a mixing pump;

a mixing conduit loop connecting the mixing pump, the eductor and the mix tank, the mixing conduit loop being connected to the source of purified water so that as water is circulated by the mixing pump through the mixing conduit loop, the dry bicarbonate material is drawn into the eductor and mixed with the water;

a circulation tank;

a transfer conduit connecting the mixing conduit loop to the circulation tank, so that a mixed bicarbonate solution can be transferred from the mixing conduit loop to the circulation tank;

a circulation pump;

a circulation supply conduit connecting the circulation tank and the circulation pump, so that mixed bicarbonate solution can be pumped from the circulation tank to the dialysis machines; and a three-way control valve connecting the mixing conduit loop to the transfer conduit.

20. A system for mixing water and an additive to form a concentrate solution, comprising:

a mix tank having an outlet;

a pump having a suction inlet connected to the outlet of the mix tank, and having a pump discharge;

an eductor, having a fluid inlet, a fluid outlet, a flow path connecting the fluid inlet and fluid outlet and having an eductor inlet connected to the flow path, the fluid inlet being connected to the pump discharge;

an additive container having an outlet connected to the eductor inlet, so that additive stored in the additive container is drawn therefrom by the flow of fluid through the flow path of the eductor;

a return line connected between the fluid outlet of the eductor and the mix tank; and a hot water source connected to the mixing system so that hot water can be circulated through the mixing system to heat disinfect the mix tank, the pump, the eductor and the additive container.

21. A system for mixing water and an additive to form a concentrate solution, comprising:

a mix tank having an outlet;

a pump having a suction inlet connected to the outlet of the mix tank, and having a pump discharge;

an eductor, having a fluid inlet, a fluid outlet, a flow path connecting the fluid inlet and fluid outlet and having an eductor inlet connected to the flow path, the fluid inlet being connected to the pump discharge;

an additive container having an outlet connected to the eductor inlet, so that additive stored in the additive container is drawn therefrom by the flow of fluid through the flow path of the eductor;

a return line connected between the fluid outlet of the eductor and the mix tank;

a circulation tank for storing mixed concentrate solution;

a transfer line for transferring mixed concentrate solution from the mix tank to the circulation tank;

at least one control valve for allowing the flow of the mixed concentrate solution to the circulation tank; and a hot water source connected to the mixing system so that hot water can be circulated through the mixing system to heat disinfect the circulation tank.

* * * * *